US011741586B2

(12) United States Patent
Jin

(10) Patent No.: US 11,741,586 B2
(45) Date of Patent: Aug. 29, 2023

(54) APPARATUS, METHOD AND RECORDING MEDIUM STORING PROGRAM FOR ASSESSING BONE AGE

(71) Applicant: BONEWISE INC., Seoul (KR)

(72) Inventor: Dong Kyu Jin, Seoul (KR)

(73) Assignee: BONEWISE INC., Seoul (KR)

( * ) Notice: Subject to any disclaimer, the term of this patent is extended or adjusted under 35 U.S.C. 154(b) by 289 days.

(21) Appl. No.: 17/273,147

(22) PCT Filed: Sep. 4, 2018

(86) PCT No.: PCT/KR2018/010322
§ 371 (c)(1),
(2) Date: Mar. 3, 2021

(87) PCT Pub. No.: WO2020/050431
PCT Pub. Date: Mar. 12, 2020

(65) Prior Publication Data
US 2022/0051379 A1 Feb. 17, 2022

(51) Int. Cl.
*G06K 9/00* (2022.01)
*G06T 5/50* (2006.01)
(Continued)

(52) U.S. Cl.
CPC .............. *G06T 5/50* (2013.01); *G06T 7/0014* (2013.01); *G06T 7/10* (2017.01); *G06T 2207/30008* (2013.01)

(58) Field of Classification Search
CPC ..... A61B 6/505; A61B 5/4504; A61B 5/4509; G06T 2207/30008; G06T 2207/30012;
(Continued)

(56) References Cited

U.S. PATENT DOCUMENTS

2003/0053673 A1   3/2003   Dewaele
2005/0157917 A1   7/2005   Saptharishi et al.
(Continued)

FOREIGN PATENT DOCUMENTS

JP    7-168944 A     7/1995
JP    2005-204695 A  8/2005
(Continued)

OTHER PUBLICATIONS

Rajitha B, Suneeta Agarwal, "Segmentation of bone pixels from EROI image using clustering method for bone age assessment", Proc. of SPIE, vol. 9789, pp. 97890H-1 to 97890H-5 (5 pages total).
(Continued)

*Primary Examiner* — Atiba O Fitzpatrick
(74) *Attorney, Agent, or Firm* — Sughrue Mion, PLLC

(57) ABSTRACT

The present disclosure proposes an apparatus for determining a bone age. The apparatus may divide an input image capturing a human body into a plurality of segmented images, determine a first segmented image having a highest priority for a first body part from the segmented images, process each of first pixels of the first segmented image based on a reference value, select a first reference image for the first body part from a reference image set, determine whether or not a partial region matching the first reference image exists in the first segmented image processed by the reference value, upon determining that the partial region exists, determine a bone age grade of the first body part based on the first reference image, and determine a bone age of the human body based on the bone age.

13 Claims, 9 Drawing Sheets

(51) Int. Cl.
*G06T 7/10* (2017.01)
*G06T 7/00* (2017.01)

(58) Field of Classification Search
CPC ....... G06T 7/0014; G06T 7/0016; G06T 7/74; G06T 2207/20021; G06V 2201/033; G16H 50/30; G16H 15/00
See application file for complete search history.

(56) References Cited

U.S. PATENT DOCUMENTS

| | | | |
|---|---|---|---|
| 2005/0259882 A1 | 11/2005 | Dewaele | |
| 2008/0139912 A1 | 6/2008 | Lee et al. | |
| 2009/0105958 A1 | 4/2009 | Thodberg | |
| 2009/0129649 A1 | 5/2009 | Djeridane | |
| 2011/0058726 A1 | 3/2011 | Markwardt et al. | |
| 2018/0232603 A1* | 8/2018 | Shim | A61B 6/00 |

FOREIGN PATENT DOCUMENTS

| | | |
|---|---|---|
| JP | 2005-218645 A | 8/2005 |
| JP | 2005-332397 A | 12/2005 |
| JP | 2008-541892 A | 11/2008 |
| JP | 2010-240290 A | 10/2010 |
| JP | 2014-000455 A | 1/2014 |
| KR | 10-2008-0065078 A | 7/2008 |
| KR | 10-2016-0140194 A | 12/2016 |
| KR | 10-1825719 B1 | 1/2018 |
| KR | 10-2018-0040287 A | 4/2018 |
| KR | 10-2018-0072549 A | 6/2018 |
| WO | 2018/057714 A1 | 3/2018 |

OTHER PUBLICATIONS

M. Niemeijer et al., "Assessing the skeletal age from a hand radiograph: automating the Tanner-Whitehouse method", Proc. of SPIE, vol. 5032, pp. 1197-1205 (9 pages total).

Ewa Pietka et al., "Feature Extraction in Carpal-Bone Analysis", IEEE Transactions on Medical Imaging, vol. 12, No. 1, Mar. 1993, pp. 44-49 (6 pages total).

Aifeng Zhang et al., "Automatic bone age assessment for young children from newborn to 7-year-old using carpal bones", Computerized Medical Imaging and Graphics, vol. 31, 2007, pp. 299-310 (12 pages total).

Extended European Search Report dated Mar. 17, 2022 from the European Patent Office in EP Application No. 18932701.8.

Notice of Reasons for Refusal dated Mar. 22, 2022 from the Japanese Patent Office in JP Application No. 2021-535477.

Korea Intellectual Property Office, Grant of Patent for KR 10-2018-0105622 dated Jun. 22, 2020.

International Search Report for PCT/KR2018/010322 dated May 23, 2019 [PCT/ISA/210].

* cited by examiner

FIG. 7
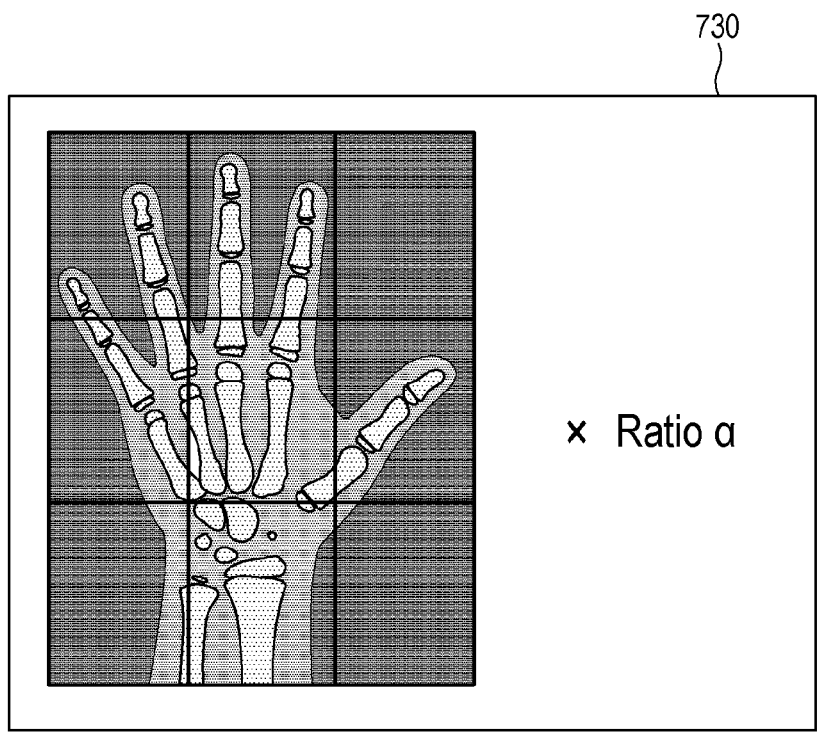
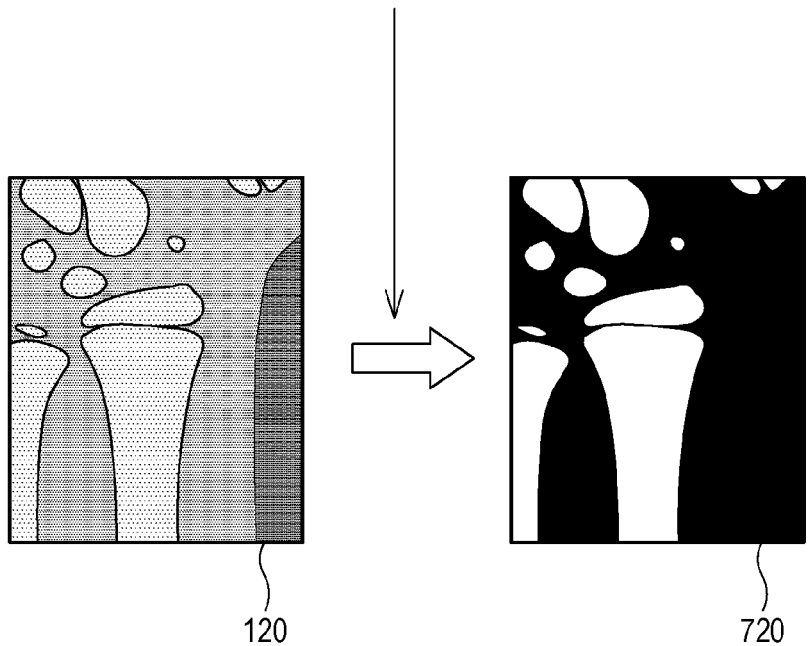

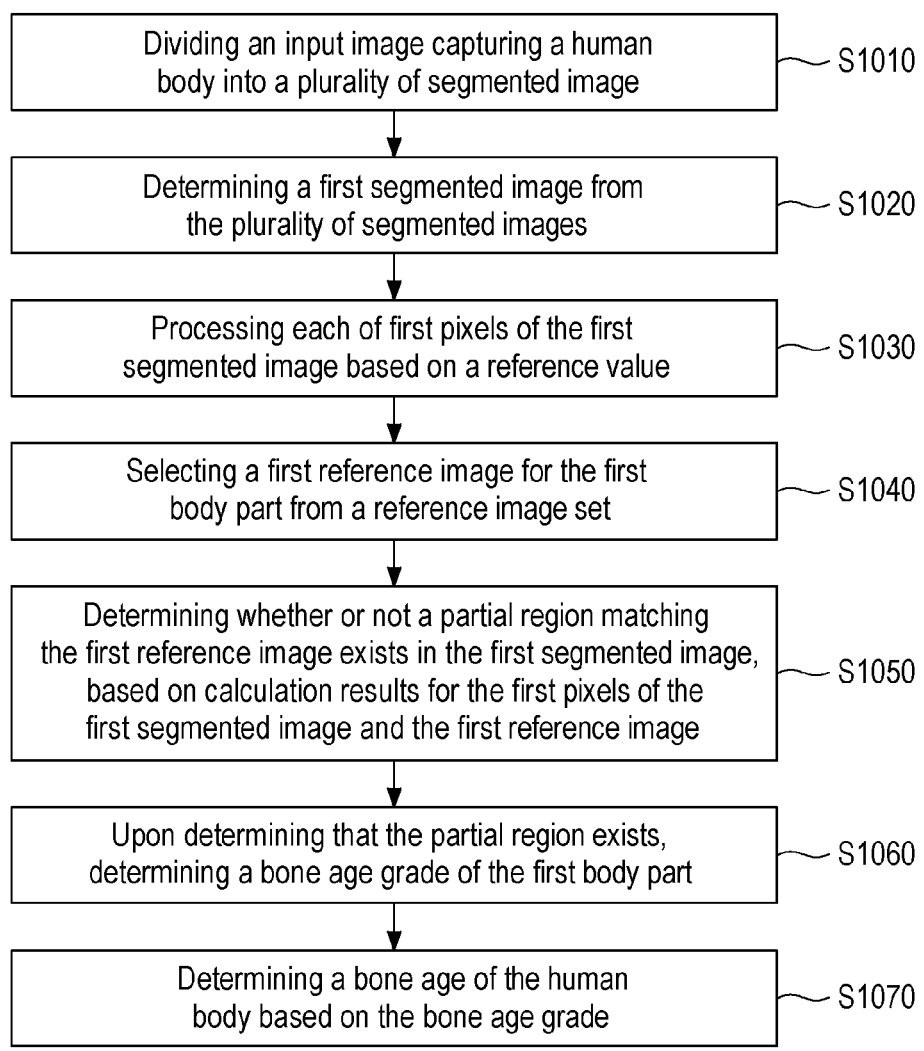

APPARATUS, METHOD AND RECORDING MEDIUM STORING PROGRAM FOR ASSESSING BONE AGE

CROSS REFERENCE TO RELATED APPLICATIONS

This application is a National Stage of International Application No. PCT/KR2018/010322 filed Sep. 4, 2018, the entire disclosure of which is incorporated herein by reference.

TECHNICAL FIELD

The present disclosure relates to a technique for bone age assessment.

BACKGROUND

A patient's bone age can be assessed from medical images (e.g., X-ray images, etc.) of the patient's body. By assessing the patient's bone age and comparing it with the patient's actual age, it is possible to determine the growth potential of the corresponding body part. In addition, from the patient's bone age, it is possible to determine whether each body part is growing normally according to the human body development process.

In order to determine a patient's bone age, the Greulich-Pyle (G&P) method or the Tanner-Whitehouse (TW) method may be used. The G&P method is a method that compares the patient's medical image with images representing the respective ages to determine an age having the closest bone maturity. The TW method is a method that analyzes and ranks the bone shape and density for each body part to determine the patient's bone age. However, both methods may have problems in that the image comparison task is performed manually, and thus, the accuracy of image comparison is poor.

SUMMARY

Various embodiments of the present disclosure provide a technique for bone age assessment capable of solving the aforementioned problems.

As one aspect of the present disclosure, an electronic apparatus for bone age assessment may be proposed. The electronic apparatus according to one aspect of the present disclosure may include: a memory configured to store a reference image set including a plurality of reference images for a plurality of body parts; and a processor communicatively connected to the memory, and configured to: divide an input image capturing a human body into a plurality of segmented images; determine a first segmented image having a highest priority for a first body part of a plurality of body parts from the plurality of segmented images; process each of first pixels of the first segmented image based on a reference value determined from all pixels of the input image; select a first reference image for the first body part from the reference image set; determine whether or not a partial region matching the first reference image exists in the first segmented image processed by the reference value, based on calculation results for the first pixels of the first segmented image processed by the reference value and second pixels of the first reference image corresponding to the first pixels; upon determining that the partial region exists, determine a bone age grade of the first body part based on the first reference image; and determine a bone age of the human body based on the bone age grade.

In one embodiment, the processor may be further configured to: process each of the first pixels of the first segmented image by setting each of pixel values of the first pixels of the first segmented image, which is smaller than the reference value, to 0 and setting each of the pixel values of the first pixels of the first segmented image, which is equal to or larger than the reference value, to a difference value between each of the pixel values and the reference value.

In one embodiment, the reference value may be an average value of all the pixels of the input image.

In one embodiment, the processor may be further configured to: multiply a pixel value of each pixel of the partial region and a pixel value of each pixel of the first reference image that corresponds to the each pixel of the partial region; determine a matching score by summing the multiplied pixel values for the partial region; and upon determining that the matching score is equal to or larger than a preset value, determine that the partial region matches the first reference image.

In one embodiment, the processor may be further configured to: determine a bone age grade of a second body part using a second segmented image having a highest priority for a second body part among the body parts and a second reference image for the second body part in the reference image set; and determine the bone age of the human body based on the bone age grade of the first body part and the bone age grade of the second body part.

In one embodiment, the processor may be further configured to: upon determining that the partial region does not exist, determine whether or not the partial region exists using a third segmented image having a priority next to the first segmented image for the first body part and the first reference image.

In one embodiment, the processor may be further configured to: upon determining that the partial region does not exist, adjust the reference value; process each of the first pixels of the first segmented image based on the adjusted reference value; and determine whether or not the partial region exists using the first segmented image processed by the adjusted reference value and the first reference image.

In one embodiment, the memory may be further configured to store a plurality of reference image sets according to races and genders, and the processor may be further configured to: determine the reference image set to be compared with the first segmented image from among the plurality of reference image sets, based on race information and gender information inputted from a user.

In one embodiment, the processor is further configured to: determine the bone age grade of the first body part according to a TW3 (Tanner-Whitehouse 3rd edition) method.

As another aspect of the present disclosure, there may be proposed a method for bone age assessment. The method according to another aspect of the present disclosure may include: dividing an input image capturing a human body into a plurality of segmented images; determining a first segmented image having a highest priority for a first body part of a plurality of body parts from the plurality of segmented images; processing each of first pixels of the first segmented image based on a reference value determined from all pixels of the input image; selecting a first reference image for the first body part from a reference image set including a plurality of reference images for each of the body parts; determining whether or not a partial region matching the first reference image exists in the first segmented image processed by the reference value, based on calculation results for the first pixels of the first segmented image processed by the reference value and second pixels of the first reference image corresponding to the first pixels; upon determining that the partial region exists, determining a bone age grade of the first body part based on the first reference image; and determining a bone age of the human body based on the bone age grade.

In one embodiment, the processing each of the first pixels of the first segmented image may include: processing each of the first pixels of the first segmented image by setting each of pixel values of the first pixels of the first segmented image, which is smaller than the reference value, to 0 and setting each of the pixel values of the first pixels of the first segmented image, which is equal to or larger than the reference value, to a difference value between each of the pixel values and the reference value.

In one embodiment, the determining whether or not the partial region matching the first reference image exists may include: multiplying a pixel value of each pixel of the partial region and a pixel value of each pixel of the first reference image that corresponds to the each pixel of the partial region; determining a matching score by summing the multiplied pixel values for the partial region; and upon determining that the matching score is equal to or larger than a preset value, determining that the partial region matches the first reference image.

As a further aspect of the present disclosure, there may be proposed a recording medium that stores a program for bone age assessment. The recording medium according to a further aspect of the present disclosure may be a non-transitory computer-readable recording medium that stores a program to be executed on a computer. The program may include executable instructions for, when executed by a processor, causing the processor to perform: dividing an input image capturing a human body into a plurality of segmented images; determining a first segmented image having a highest priority for a first body part of a plurality of body parts from the plurality of segmented images; processing each of first pixels of the first segmented image based on a reference value determined from all pixels of the input image; selecting a first reference image for the first body part from a reference image set including a plurality of reference images for each of the body parts; determining whether or not a partial region matching the first reference image exists in the first segmented image processed by the reference value, based on calculation results for the first pixels of the first segmented image processed by the reference value and second pixels of the first reference image corresponding to the first pixels; upon determining that the partial region exists, determining a bone age grade of the first body part based on the first reference image; and deriving a bone age of the human body based on the bone age grade.

In one embodiment, the processing each of the first pixels of the first segmented image may include: processing each of the first pixels of the first segmented image by setting each of pixel values of the first pixels of the first segmented image, which is smaller than the reference value, to 0 and setting each of the pixel values of the first pixels of the first segmented image, which is equal to or larger than the reference value, to a difference value between each of the pixel values and the reference value.

In one embodiment, the determining whether or not the partial region matching the first reference image exists may include: multiplying a pixel value of each pixel of the partial region and a pixel value of each pixel of the first reference image that corresponds to the each pixel of the partial region; determining a matching score by summing the multiplied pixel values for the partial region; and upon determining that the matching score is equal to or larger than a preset value, determining that the partial region matches the first reference image.

In one embodiment, the program may include executable instructions for, when executed by the processor, causing the processor to further perform: upon determining that the partial region does not exist, determining whether or not the partial region exists using a third segmented image having a priority next to the first segmented image for the first body part and the first reference image.

In one embodiment, the program may include executable instructions for, when executed by the processor, causing the processor to further perform: upon determining that the partial region does not exist, adjusting the reference value; processing each of the first pixels of the first segmented image based on the adjusted reference value; and determining whether or not the partial region exists using the first segmented image processed by the adjusted reference value and the first reference image.

According to various embodiments of the present disclosure, the bone age of a patient can be assessed by automatically comparing the image of the human body of the patient with the reference image of a body part.

According to various embodiments of the present disclosure, image comparison and bone age assessment can be performed accurately by comparing the shape between the image of the human body and the reference image through pattern matching for each pixel.

According to various embodiments of the present disclosure, the amount of computation consumed in image comparison can be reduced by dividing the image of the human body into individual sections to perform image comparison, or by prioritizing the individual sections.

BRIEF DESCRIPTION OF DRAWINGS

FIG. 7 illustrates a process of adjusting a reference value when a matching partial region does not exist, according to an embodiment of the present disclosure.

FIG. 10 illustrates a bone age assessment method that may be performed by the electronic apparatus 200 according to an embodiment of the present disclosure.

DETAILED DESCRIPTION

Figure 1:
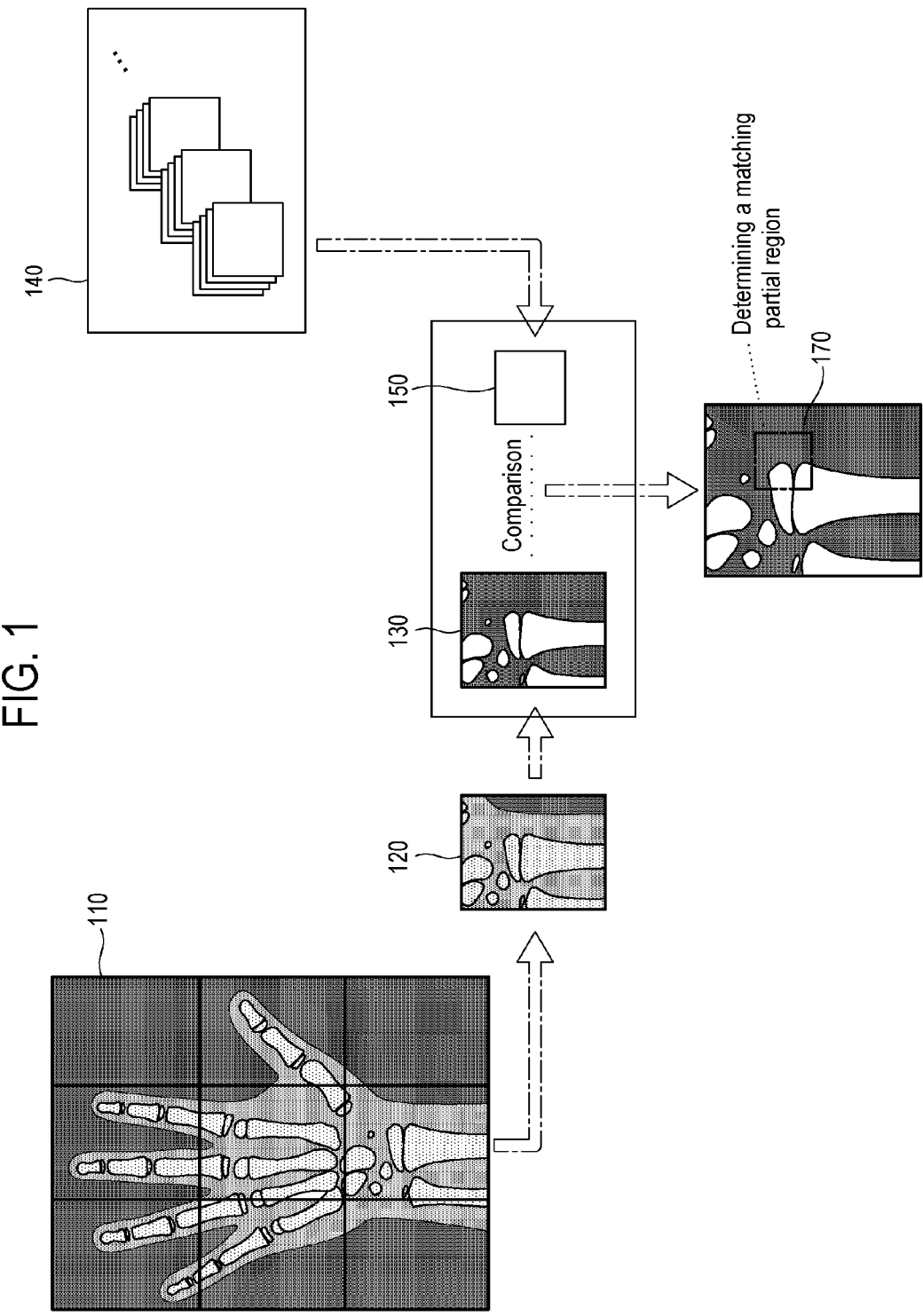
FIG. 1 illustrates an operation of an electronic apparatus according to an embodiment of the present disclosure.

The various embodiments described herein are exemplified for the purpose of clearly describing the technical idea of the present disclosure, and are not intended to limit the technical idea of the present disclosure to specific embodiments. The technical idea of the present disclosure includes various modifications, equivalents, alternatives of each of the embodiments described in this document, and embodiments selectively combined from all or part of the respective embodiments. In addition, the scope of the technical idea of the present disclosure is not limited to various embodiments or detailed descriptions thereof presented below.

The terms used herein, including technical or scientific terms, may have meanings that are generally understood by a person having ordinary knowledge in the art to which the present disclosure pertains, unless otherwise specified.

As used herein, the expressions such as "include," "may include," "provided with," "may be provided with," "have," and "may have" mean the presence of subject features (e.g., functions, operations, components, etc.) and do not exclude the presence of other additional features. That is, such expressions should be understood as open-ended terms that imply the possibility of including other embodiments.

A singular expression can include meanings of plurality, unless otherwise mentioned, and the same is applied to a singular expression stated in the claims.

The terms "first," "second," etc. used herein are used to distinguish a plurality of components from one another, and are not intended to limit the order or importance of the relevant components.

As used herein, the expressions such as "A, B and C," "A, B or C," "A, B and/or C," "at least one of A, B and C," "at least one of A, B or C," "at least one of A, B and/or C," "at least one selected from A, B and C," "at least one selected from A, B or C," and "at least one selected from A, B and/or C" may mean each of the listed items or all possible combinations of the listed items. For example, the expression "at least one selected from A and B" may refer to (1) at least one A, (2) at least one B, and (3) both at least one A and at least one B.

The term "part" used in these embodiments means a software component or hardware component, such as a field-programmable gate array (FPGA) and an application specific integrated circuit (ASIC). However, a "part" is not limited to software and hardware, it may be configured to be an addressable storage medium or may be configured to run on one or more processors. For example, a "part" may include components, such as software components, object-oriented software components, class components, and task components, as well as processors, functions, attributes, procedures, subroutines, segments of program codes, drivers, firmware, micro-codes, circuits, data, databases, data structures, tables, arrays, and variables.

The expression "based on" or "according to" used herein is used to describe one or more factors that influence a decision, an action of judgment or an operation described in a phrase or sentence including the relevant expression, and this expression does not exclude additional factor influencing the decision, the action of judgment or the operation.

As used herein, the expression that a certain component (e.g., a first component) is "connected" to another component (e.g., a second component) may mean that the certain component is not only connected or coupled to another component directly, but also connected or coupled via a new other component (e.g., a third component).

As used herein, the expression "configured to" may have a meaning such as "set to," "having the ability to," "modified to," "made to," "capable of," or the like depending on the context.

Hereinafter, various embodiments of the present disclosure will be described with reference to the accompanying drawings. In the accompanying drawings and the descriptions of the drawings, the same reference numerals may be assigned to the same or substantially equivalent elements. Furthermore, in the following description of various embodiments, redundant descriptions of the same or corresponding elements may be omitted. However, this does not mean that the elements are not included in the embodiments.

FIG. 1 illustrates an operation of an electronic apparatus (not shown) according to an embodiment of the present disclosure. A bone age assessment apparatus according to the present disclosure may be implemented by an electronic apparatus according to various embodiments. The electronic apparatus according to various embodiments of the present disclosure may determine a bone age through a comparison of an input image obtained by capturing a human body and a reference image for each of body parts. The electronic apparatus to be described below may include one or more computers and/or servers. The computers and/or the servers may be communicatively connected via, for example, a network. Each of the computers and/or each of the servers may include one or more processors and/or one or more memories (or storage devices).

Specifically, the electronic apparatus may acquire an input image 110 obtained by capturing a human body. The input image 110 may be a medical image (e.g., an X-ray image) of a part of the human body, and may be, for example, an image obtained by capturing a patient's hand. The electronic apparatus may divide the input image 110 into a plurality of segmented images. The input image 110 may be divided in various ways according to the intention of a practitioner. In one embodiment, the electronic apparatus may equally divide the input image 110 into nine rectangular segmented images.

The electronic apparatus may select a first segmented image 120 from the segmented images. The selected first segmented image 120 may be a segmented image having a highest priority for a first body part, which is one of the body parts. In the present disclosure, the priority of the segmented image for a specific body part may mean a degree of probability that the segmented image includes an image of the specific body part. That is, the segmented image 120 having a highest priority for a specific body part (e.g., a first body part) means that, among the segmented images, the segmented image 120 has the highest probability of including an image of the specific body part. In the input image 110 obtained by capturing a human body (e.g., the hand), depending on the shape and size of the human body (e.g., the hand) and the location of the human body at the time of imaging, which of the segmented images of the input image includes a specific body part (e.g., the wrist joint) may vary. However, statistically, the specific body part (e.g., the wrist joint) may have a higher probability of being included in the specific segmented image 120 than other segmented images. Based on the probability that each of the body parts is included, each segmented image may have a priority for each of the body parts. In the illustrated embodiment, it can be said that the segmented image 120 has the highest priority for the first body part.

The electronic apparatus may process each of first pixels of the first segmented image 120 based on a reference value determined from all pixels of the input image 110. Each of the pixels of the input image 110 may have a pixel value. The reference value may be determined by a predetermined manner based on the pixel values of the pixels of the input image 110. The electronic apparatus may compare the pixel values of the first pixels of the first segmented image 120 with the reference value, and may adjust the pixel values of the first pixels according to a predetermined criterion. A specific method of processing the pixel values of the first pixels of the first segmented image 120 will be described later.

Meanwhile, the electronic apparatus may select a first reference image 150 for the first body part from one reference image set 140. The electronic apparatus may store one or more reference image sets, and each of the reference image sets may include one or more reference images.

In the present disclosure, the reference image may be an image representing a reference form of one body part at a specific bone age. Each of the reference images may be associated with one specific body part and a specific bone age grade of the specific body part. The reference image may be compared with the input image (or the segmented image), and may be used to determine a body part represented by a specific region in the input image (or the segmented image) and the bone age of the determined body part. For example, if a partial region corresponding to one reference image exists in the input image (or the segmented image), the partial region may be a region corresponding to the body part (e.g., the wrist joint) represented by the reference image. At the same time, the body part (e.g., the wrist joint) represented by the partial region may be determined to have a bone age (e.g., a bone age of 5 years old) indicated by the reference image. In the present disclosure, the reference image set may be a set of reference images classified according to a specific race and/or a gender. One reference image set may include reference images for a plurality of body parts and a plurality of bone ages in the corresponding race and/or gender.

The electronic apparatus may compare the first segmented image 130, which is the first segmented image 120 processed by the reference value, and the selected first reference image 150. In the comparison process, the electronic apparatus may perform a pixel-by-pixel calculation between first pixels of the first segmented image 130 and second pixels of the first reference image 150 corresponding to the first pixels. Based on the calculation result, it may be possible to determine whether a partial region 170 matching the first reference image 150 exists in the first segmented image 130. A specific process of the pixel-by-pixel calculation will be described later.

If it is determined that the partial region 170 exists, the electronic apparatus may determine the bone age grade of the first body part represented by the partial region 170, based on the information associated with the first reference image 150 used in the comparison process. That is, if the partial region 170 matching the first reference image 150 exists, it can be confirmed that the partial region 170 is a region representing the first body part indicated by the first reference image 150. In addition, the bone age grade of the first body part may be determined as a bone age grade corresponding to the first reference image 150.

The electronic apparatus may determine the bone age of the human body (e.g., the hand) according to the bone age grade determined for the first body part. In one embodiment, the electronic apparatus may determine the bone age of the human body (e.g., the hand) by determining the bone age grades for a plurality of body parts as well as the first body part, and combining the determined bone age grades.

Figure 2:
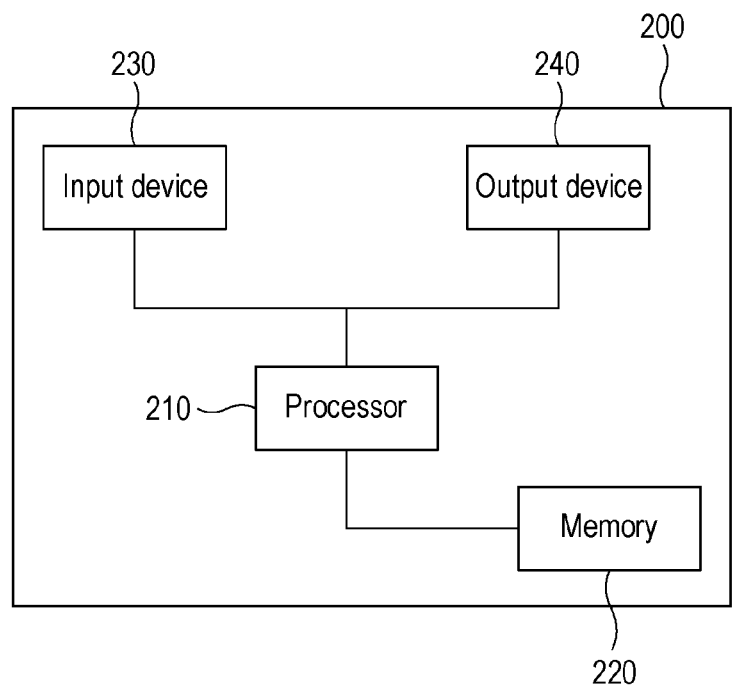
FIG. 2 is a block diagram of the electronic apparatus 200 according to various embodiments of the present disclosure.

FIG. 2 is a block diagram of an electronic apparatus 200 according to various embodiments of the present disclosure. In one embodiment, the electronic apparatus 200 may include a processor 210, a memory 220, an input device 230 and/or an output device 240. In one embodiment, at least one of these components of the electronic apparatus 200 may be omitted or another component may be added to the electronic apparatus 200. Additionally or alternatively, some components may be implemented in an integrated form, or may be implemented as a singular entity or plural entities. In particular, the input device 230 and/or the output device 240 may be omitted from the electronic apparatus 200. At least some of the internal and external components of the electronic apparatus 200 may be connected to each other through a bus, a general purpose input/output (GPIO), a serial peripheral interface (SPI), a mobile industry processor interface (MIPI), or the like to exchange data and/or signals.

The processor 210 may drive software (e.g., a program) to control at least one component of the electronic apparatus 200 connected to the processor 210. In addition, the processor 210 may perform various operations related to the present disclosure, such as calculation, treatment, data generation, processing, and the like. In addition, the processor 210 may load data or the like from the memory 220, or may store data in the memory 220.

The processor 210 may divide the input image capturing the human body into a plurality of segmented images. The processor 210 may determine (select) a first segmented image having a highest priority for a first body part from among the segmented images. The processor 210 may process each of a plurality of first pixels of the determined first segmented image based on the above-described reference value. In addition, the processor 210 may select a first reference image for the first body part from one reference image set.

The processor 210 may compare the first segmented image processed by the reference value with the first reference image. Specifically, the processor 210 may calculate each of a plurality of first pixels of the first segmented image and each of a plurality of second pixels of the first reference image corresponding to each of the first pixels. The processor 210 may determine whether a partial region matching the first reference image exists in the first segmented image, based on the calculation result.

If it is determined that the partial region exists, the processor 210 may determine that the partial region is a region representing the first body part, and may determine the bone age grade associated with the first reference image as the bone age grade of the first body part. The processor 210 may determine a bone age of the human body (e.g., the hand) based on the determined bone age grade. In one embodiment, the processor 210 may use various methods when determining the bone age grade of the first body part based on the first reference image. For example, when determining the bone age grade, a TW3 (Tanner-Whitehouse 3rd edition) method may be used. Data required to perform the method of determining each bone age grade (e.g., a bone shape atlas) may be stored in the memory 220.

The memory 220 may store various types of data. The data stored in the memory 220 may be data acquired, processed or used by at least one component of the electronic apparatus 200, and may include software (e.g., a program). The memory 220 may include a volatile memory and/or a nonvolatile memory. The memory 220 may store one or more reference image sets.

In the present disclosure, the program is software stored in the memory 220, and may include an operating system for controlling resources of the electronic apparatus 200, an application, and/or middleware for providing various functions to the application so that the application may utilize the resources of the electronic apparatus. The application may be a concept including an application running on a mobile device.

In one embodiment, the electronic apparatus 200 may further include an input device 230. The input device may be a device that receives data to be transmitted from the outside of the electronic apparatus 200 to at least one component of the electronic apparatus 200. For example, the input device may include a mouse, a keyboard, a touch pad, and the like.

In one embodiment, the electronic apparatus 200 may further include an output device 240. The output device may be a device that provides various data, such as an inspection result of the electronic apparatus 200, an operation state thereof, and the like, to a user in a visual form. For example, the output device may include a display, a projector, a hologram, and the like.

In one embodiment, the electronic apparatus 200 may further include a communication interface (not shown). The communication interface may perform wireless or wired communication between the electronic apparatus 200 and a server, or between the electronic apparatus 200 and another external electronic apparatus. For example, the communication interface may perform wireless communication according to a method such as LTE (Long-Term Evolution), LTE-A (LTE Advance), CDMA (Code Division Multiple Access), WCDMA (Wideband CDMA), WiBro (Wireless Broadband), WiFi (Wireless Fidelity), Bluetooth, NFC (Near Field Communication), GPS (Global Positioning System), or GNSS (Global Navigation Satellite System). For example, the communication interface may perform wired communication according to a method such as USB (Universal Serial Bus), HDMI (High Definition Multimedia Interface), RS-232 (Recommended Standard-232), or POTS (Plain Old Telephone Service). In one embodiment, the processor 210 may obtain information from the server by controlling the communication interface. The information obtained from the server may be stored in the memory 220. In one embodiment, the information obtained from the server may include at least one reference image set.

In one embodiment, the electronic apparatus 200 may be an apparatus of various types. For example, the electronic apparatus 200 may be a portable communication apparatus, a computer apparatus, a portable multimedia apparatus, a wearable apparatus, or an apparatus obtained by combining the aforementioned apparatuses. The electronic apparatus 200 of the present disclosure is not limited to the above-described apparatuses.

Various embodiments of the electronic apparatus 200 according to the present disclosure may be combined with each other. The respective embodiments may be combined according to the number of cases. Embodiments of the electronic apparatus 200 obtained by such combination also fall within the scope of the present disclosure. Furthermore, the internal/external components of the electronic apparatus 200 according to the present disclosure described above may be added, changed, replaced, or deleted depending on the embodiments. In addition, the internal/external components of the electronic apparatus 200 described above may be implemented as hardware components.

Figure 3:
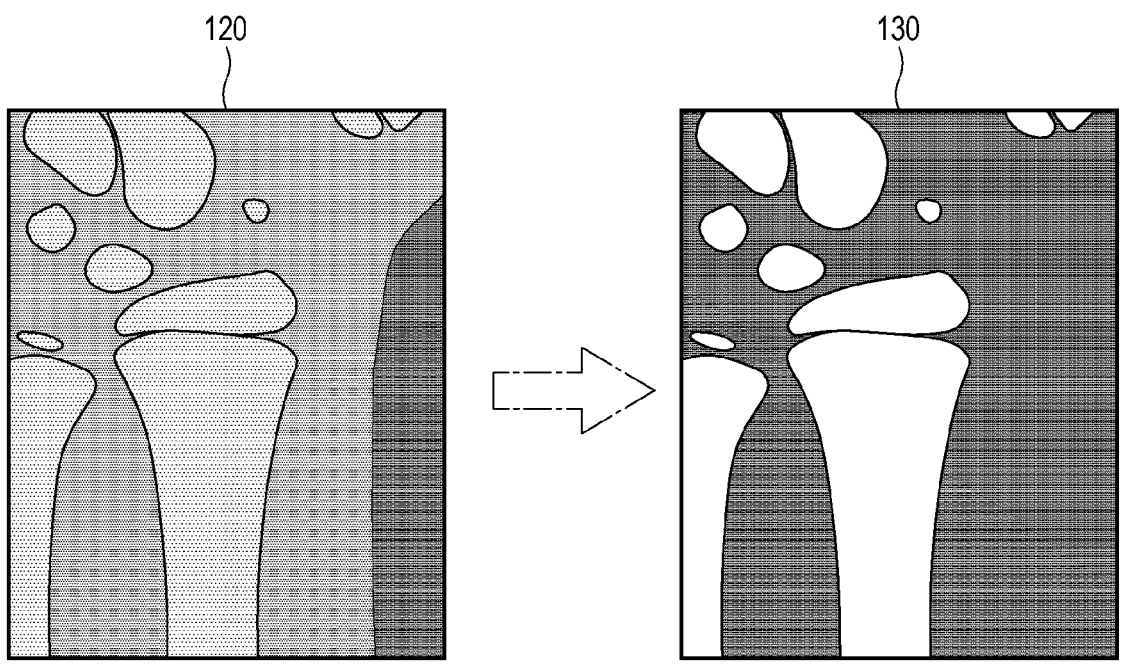
FIG. 3 illustrates a process of processing pixels of a segmented image according to an embodiment of the present disclosure.

FIG. 3 illustrates a process of processing pixels of a segmented image according to an embodiment of the present disclosure. As described above, the processor 210 may process each of a plurality of first pixels of the first segmented image based on the reference value determined from all the pixels of the input image. In the present disclosure, the pixels of the segmented image may be processed in various ways prior to the process of comparison with the reference image.

In one embodiment, the processor 210 may adjust each of the pixel values of the first pixels of the first segmented image 120 based on the reference value. Specifically, the processor 210 may set the pixel value of each of the first pixels of the first segmented image 120, which is smaller than the above-described reference value, to 0. In addition, the processor 210 may set the pixel value of each of the first pixels of the first segmented image 120, which is equal to or larger than the above-described reference value, to a difference value between the reference value and the corresponding pixel value.

Generally, the input image (or segmented image) such as an X-ray image or the like is captured in black and white. Soft tissues such as the skin, the flesh and the like may appear in gray on the input image, and hard tissues such as the bone and the like may appear in white on the input image. If the pixel values are adjusted according to the reference value as described above, a soft tissue portion appearing in gray becomes black because the pixel value thereof becomes 0. Thus, the shape of the soft tissue portion may disappear from the input image. On the other hand, a hard tissue appearing in white retains its shape even after the above-described processing. As a result, it is possible to reduce errors due to the soft tissue in the process of comparing with the reference image to be performed later. This makes it possible to perform clear comparison between the actual bone shape and the reference image. As shown, the first segmented image 120 may be processed like the first segmented image 130 according to the above-described process. It can be said that the first segmented image 130 after processing does not reveal the soft tissue as compared with the first segmented image 120 before processing.

In one embodiment, the reference value may be an average value of the pixel values of all the pixels of the input image. In one embodiment, the reference value may be a value determined by the processor 210, or may be a value determined in advance, stored in the memory 220 and loaded by the processor 210 as needed. In one embodiment, the processor 210 may set the pixel value of each of the first pixels of the first segmented image 120, which is equal to or larger than the aforementioned reference value, to a maximum value (e.g., 100). In one embodiment, the processor 210 may not adjust the pixel value of each of the first pixels of the first segmented image 120, which is equal to or larger than the aforementioned reference value, and may leave the original pixel value as it is.

Figure 4:
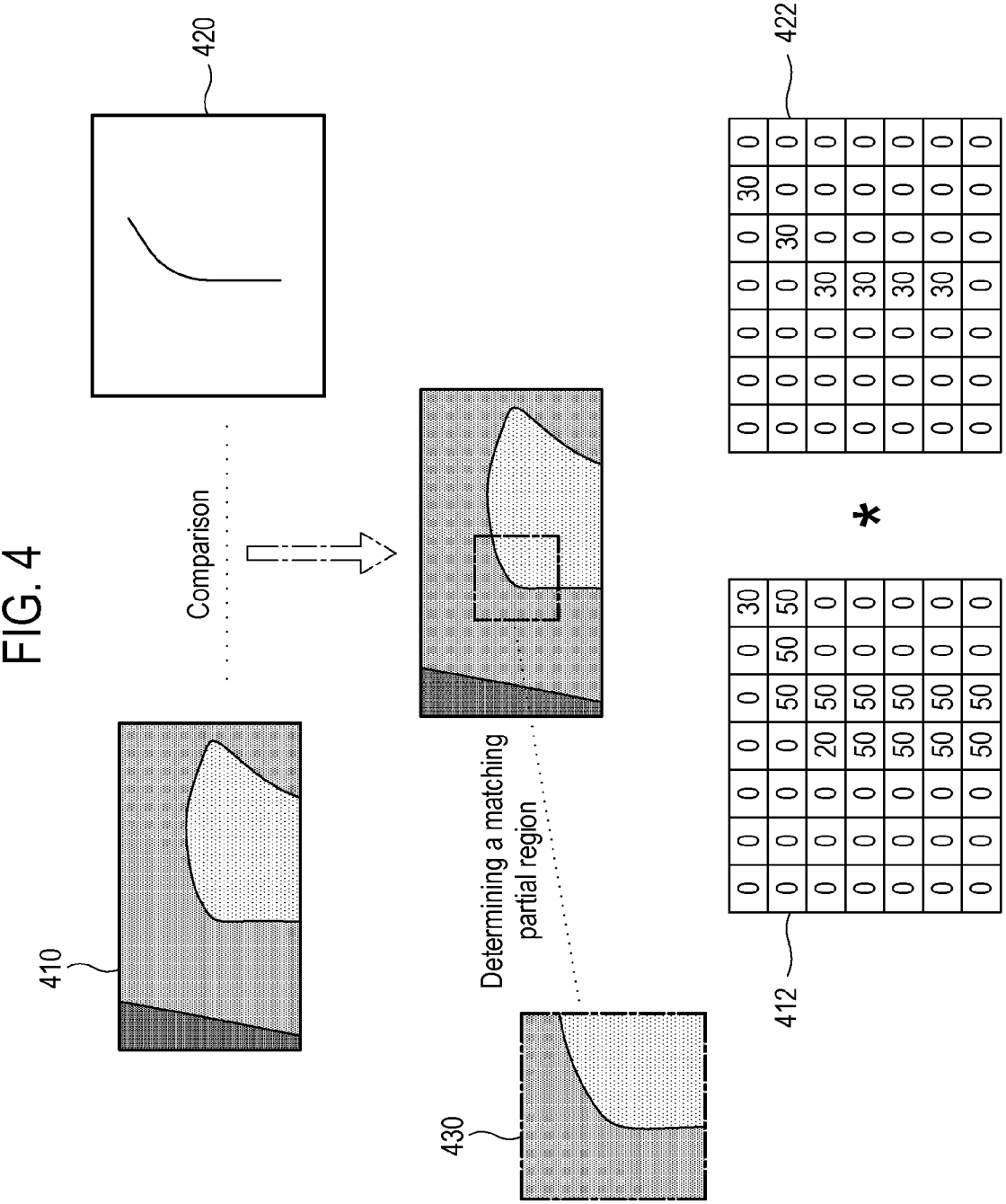
FIG. 4 illustrates a process of finding a partial region matching a reference image in a segmented image according to an embodiment of the present disclosure.

FIG. 4 illustrates a process of finding a partial region that matches a reference image in a segmented image according to an embodiment of the present disclosure. As described above, the processor 210 may compare the first segmented image processed by the reference value with the first reference image. The processor 210 may calculate each of a plurality of first pixels of the first segmented image and each of a plurality of second pixels of the first reference image corresponding to each of the first pixels. Based on the calculation result, the processor 210 may determine whether or not a partial region matching the first reference image exists in the first segmented image.

Specifically, the processor 210 may compare the first segmented image 410 processed by the above-described reference value with the above-described first reference image 420. The first reference image 420 may be an image representing the shape of the first body part, which is one of the body parts, at a specific bone age. In the comparison process, the processor 210 may scan the first segmented image 410 with the first reference image 420 to determine whether or not a partial region having a shape matching the first reference image 420 exists in the first segmented image 410.

The processor 210 may determine whether or not a partial region 430 matching the first reference image 420 exists in the first segmented image 410. The determination of whether or not one partial region matches the first reference image 420 may be performed based on the calculation result obtained by performing pixel-by-pixel calculation between the partial region and the first reference image 420.

This pixel-by-pixel calculation may be performed according to various embodiments. In one embodiment, the processor 210 may multiply each pixel value of each pixel of one partial region and each pixel value of the each corresponding pixel of the first reference image, and may determine whether or not the partial region matches the first reference image based on a matching score determined by summing the multiplication results for the respective pixel values. Specifically, the processor 210 may multiply a pixel value of each pixel of one partial region (the region indicated by a rectangle in FIG. 4) of the first segmented image 410 processed by the reference value and a pixel value of each pixel of the first reference image 420 that corresponds to the each pixel of the one partial region. In this regard, the resolutions, i.e., the numbers of horizontal and vertical pixels, of the partial region and the first reference image 420 may be equal to each other. The corresponding pixels may mean pixels positioned at the same location in the partial region and the first reference image 420. Thereafter, the processor 210 may determine the matching score by summing all the multiplication results for the respective pixel values. When the determined matching score is equal to or larger than a preset value, the processor 210 may determine that the one partial region is a region (i.e., the partial region 430) that matches the first reference image 420.

For example, the pixel values of the partial region of the first segmented image processed by the reference value may appear as the illustrated pixel value distribution 412. Further, the pixel values of the first reference image may appear as the illustrated pixel value distribution 422. The processor 210 may multiply the pixel values of the corresponding pixels, sum the multiplied pixel values for each of the corresponding pixels, and determine a matching score. That is, in this case, the matching score may be determined as (50*30)+(50*30)+(50*30)+(20*30)+(50*30)=6600. Values that do not affect the matching score due to multiplication with the pixel value of 0 are excluded from the equation. If the preset reference value is, for example, 5000, the corresponding partial region may be determined as a partial region matching the first reference image.

In one embodiment, the preset value to be compared with the matching score may be stored in the above-described memory 220. In one embodiment, the processor 210 may not compare the determined matching score with the preset value, but may determine the partial region of the first segmented image 410 having the highest matching score, as a partial region 430 matching the first reference image 420. In one embodiment, a pattern matching algorithm different from the aforementioned one may be used in order to determine the partial region matching the first reference image 420.

Figure 5:
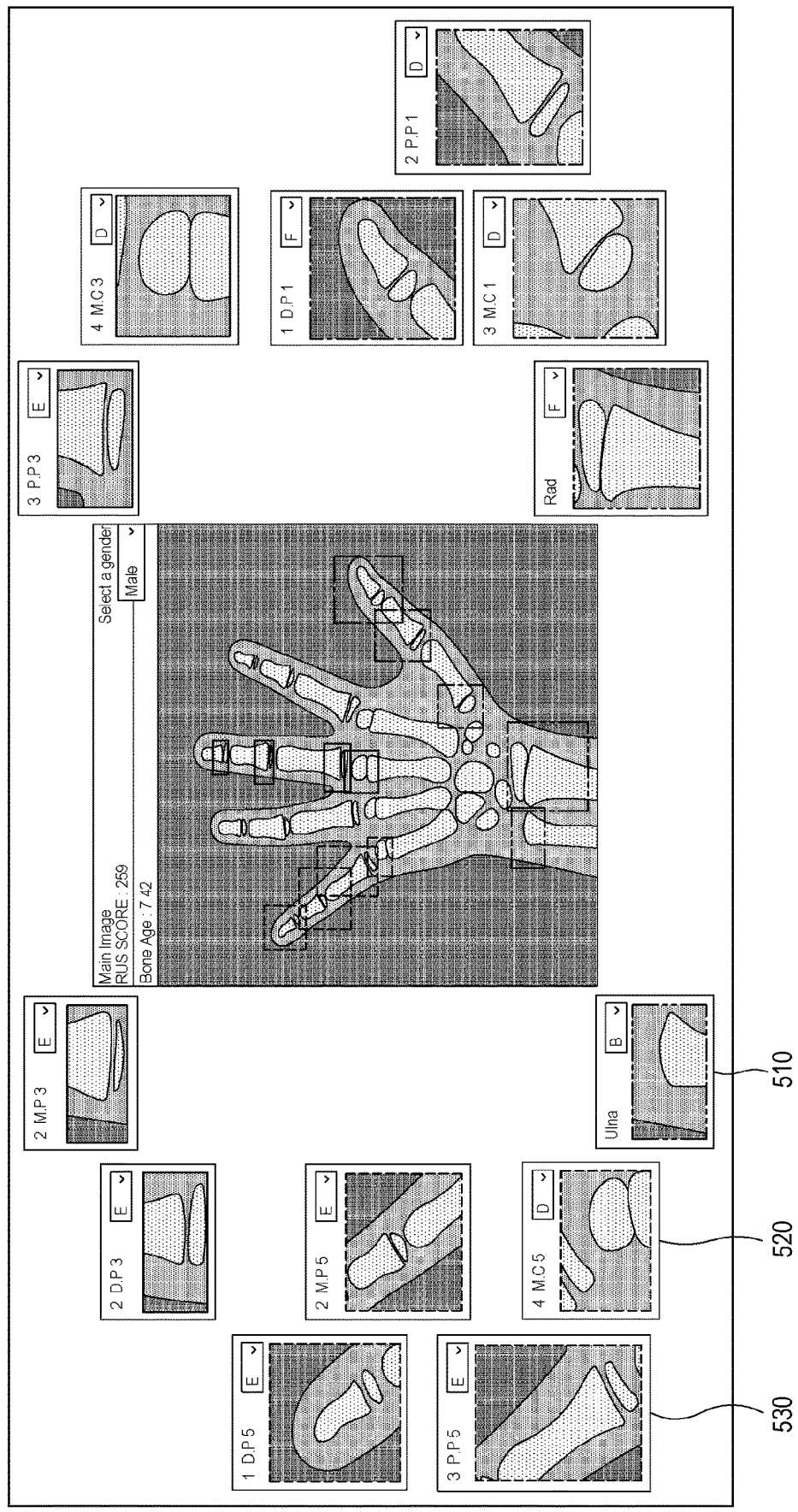
FIG. 5 illustrates a process of determining a bone age of a human body based on bone age grades for a plurality of body parts, according to an embodiment of the present disclosure.

FIG. 5 illustrates a process of determining a bone age of a human body based on bone age grades for a plurality of body parts, according to an embodiment of the present disclosure. In one embodiment, the electronic apparatus 200 may determine a bone age grade for each of a plurality of body parts (e.g., the thumb joint, the wrist joint, etc.) of a human body (e.g., the hand) in the same manner as described above, and may determine a bone age of the whole human body (e.g., the hand) in consideration of the bone age grade for each of the body parts.

The human body subject to bone age assessment may include a plurality of body parts. The plurality of body parts may be major parts of the human body that may affect the final determination of the bone age of the human body. For example, in the case of the hand, about 13 major body parts may be used for image comparison to determine a bone age. The above-described reference image set may include reference images for a plurality of body parts corresponding to individual bone ages.

As described in the method of determining the bone age grade for the first body part according to the above-described process, the processor 210 may determine a bone age grade for another body part, for example, a second body part. The processor 210 may determine a second segmented image having a highest priority for the second body part among the plurality of body parts. The processor 210 may process pixels of the second segmented image based on the reference value, and may compare the processed second segmented image with a second reference image for the second body part. The comparison process may be performed in the same way as described above. Thus, the processor 210 may determine the bone age grade of the second body part. The processor 210 may determine a bone age of the human body by considering the bone age grade determined for the first body part, the bone age grade determined for the second body part, and/or the bone age grades determined for other body parts.

For example, the processor 210 may first determine bone age grades for illustrated body parts 510, 520, 530, etc. The body part 510, the body part 520 and the body part 530 may be determined to have bone age grades B, D and E, respectively. Bone age grades for other body parts can be determined in the same manner. The processor 210 may determine an overall score of the corresponding human body based on the corresponding bone age grades. In the illustrated embodiment, the overall score is determined to be 259. Accordingly, the bone age of the human body may be determined to be 7.42 years old. The process of determining the bone age from the overall score may be performed based on the information (e.g., a look-up table) previously stored in the memory 220.

In one embodiment, the processor 210 may determine a bone age based on only the bone age grades for some body parts selected according to a predetermined criterion, instead of the bone age grades for all of the plurality of body parts. In one embodiment, the processor 210 may determine a bone age by giving a weight to the bone age grades of some body parts according to a predetermined criterion. This is because the respective body parts may have different degrees of influence on the determination of the total bone age. In one embodiment, when the bone age grade of one specific body part deviates by a predetermined amount or more from the bone age grades of other body parts, the processor 210 may determine that the bone age grade determined for the specific body part is an error, and may exclude the bone age grade of the specific body part when determining the total bone age.

Figure 6:
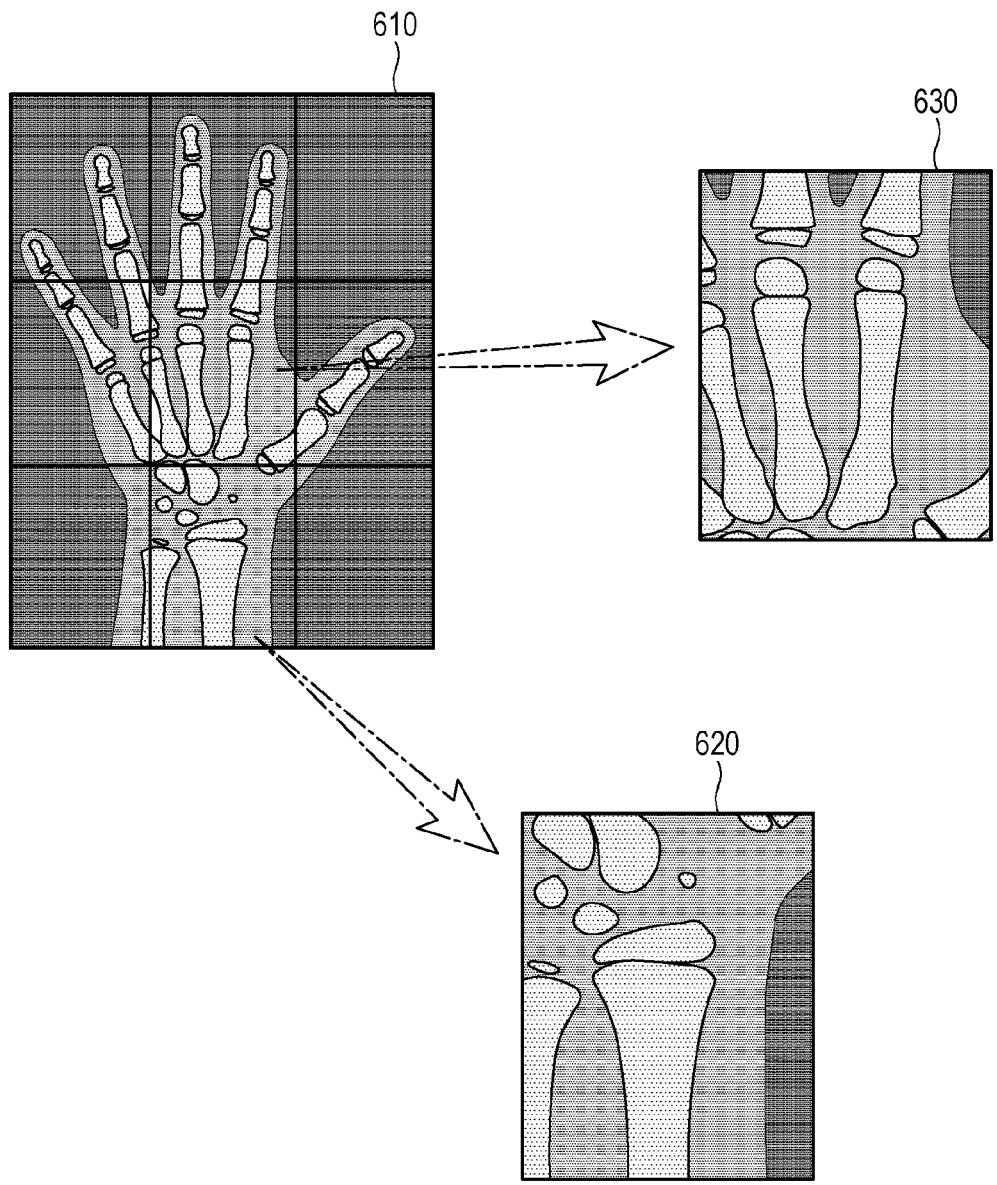
FIG. 6 illustrates a process of selecting a segmented image to be compared with a next reference image according to priority, according to an embodiment of the present disclosure.

FIG. 6 illustrates a process of selecting a segmented image to be compared with a next reference image depending on a priority, according to an embodiment of the present disclosure. As described above, each segmented image has a priority to perform image comparison for one body part according to the probability of including the one body part. For example, in an input image 610 for the human body (e.g., the hand), the probability that one body part (e.g., the wrist joint) is included in one specific segmented image 620 of the input image 610 may be high. Although there may be errors depending on the shape and size of the human body (e.g., the hand) and the location of the human body at the time of image capturing, statistically, the probability that one body part (e.g., the wrist joint) is included in one specific segmented image 620 may be higher than the probability that one body part is included in other segmented images. That is, according to the probability of one body part being included in each segmented image, the segmented image may have a priority to perform image comparison for the corresponding body part.

In one embodiment, if the electronic apparatus 200 fails to find a partial region matching the first reference image from the first segmented image having the highest priority for the first body part, the electronic apparatus 200 may continue to find a matching partial region in a third segmented image that has a next priority (the second highest priority) for the first body part. Specifically, the processor 210 may determine that a partial region matching the first reference image does not exist in the first segmented image 620 processed by the reference value. In this case, the processor 210 may determine a third segmented image 630 having a priority next to the first segmented image for the first body part if it is determined that the partial region does not exist. As described above, the processor 210 may process the pixel values of the third segmented image 630 based on the reference value. The processor 210 may compare the processed third segmented image 630 with the first reference image to determine whether a partial region matching the first reference image exists in the third segmented image 630. If the corresponding partial region exists in the third segmented image 630, it may be determined that the corresponding partial region represents the first body part and further that the first body part has a bone age grade associated with the first reference image.

In one embodiment, if a partial region matching the first reference image does not exist even in the segmented image having the next priority (e.g., the third segmented image), the processor 210 may continue to find a matching partial region in a segmented image having a priority next to the third segmented image for the first body part. Thereafter, according to the priority for the first body part, the processor 210 may sequentially search for the segmented images.

In one embodiment, the processor 210 may not perform an operation of comparison with the first reference image in the segmented images having priorities lower than a predetermined priority for one body part. This is because, for example, if a shape matching the first reference image is found in a place where the probability of existence of a partial region matching the first body part is statistically low, the shape may indicate a body part other than the first body part, or may be an arbitrarily occurring error in the input image.

FIG. 7 illustrates a process of adjusting a reference value when a matching partial region does not exist, according to an embodiment of the present disclosure. In one embodiment, if it is determined that the partial region does not exist, the electronic apparatus 200 may adjust the above-described reference value, may reprocess the pixel values of the first segmented image, and may compare the first segmented image with the first reference image again. By processing the pixel values by the adjusted reference value, the black and white contrast of the first segmented image may be even clearer in some embodiments. Accordingly, it is possible to further reduce errors in the operation of matching with the first reference image.

Specifically, if it is determined that the partial region matching the first reference image does not exist in the first segmented image processed by the reference value, the processor 210 may adjust the reference value used for processing the first segmented image. As described above, the reference value is a value determined based on all the pixels of the input image, and may be an average value of all the pixels of the input image in one embodiment. During the adjustment process, the processor 210 may use a value obtained by applying a predetermined ratio α to the previously used reference value as a new reference value (730). That is, the new reference value may be a value obtained by multiplying an existing reference value (e.g., 50, 55, or the like) and a predetermined ratio (e.g., 0.75, 1.25, or the like).

The processor 210 may process the first segmented image 120 by using the new reference value (adjusted reference value). The processing of the first segmented image by the new reference value may follow one of the embodiments of processing the first segmented image by the reference value described above. The processor 210 may search for a partial region matching the first reference image in the first segmented image 720 processed by the adjusted reference value, and may determine whether or not the corresponding partial region exists. If a matching partial region is found in the first segmented image 720, the processor 210 may determine a bone age grade of the corresponding first body part using the first reference image.

In one embodiment, various methods may be used to adjust the reference value. In one embodiment, the predetermined ratio used to adjust the reference value may be larger than or smaller than 1. In one embodiment, instead of multiplying the existing reference value and the predetermined ratio, a reference value may be determined from the pixel values of the input image in a different manner than the existing reference value, and may be used as a new reference value. In one embodiment, the first segmented image 120 before processing may not be processed with the adjusted reference value. Instead, the first segmented image 120 before processing may be processed by the existing reference value, and then the processed first segmented image 120 may be further processed by the adjusted reference value.

Figure 8:
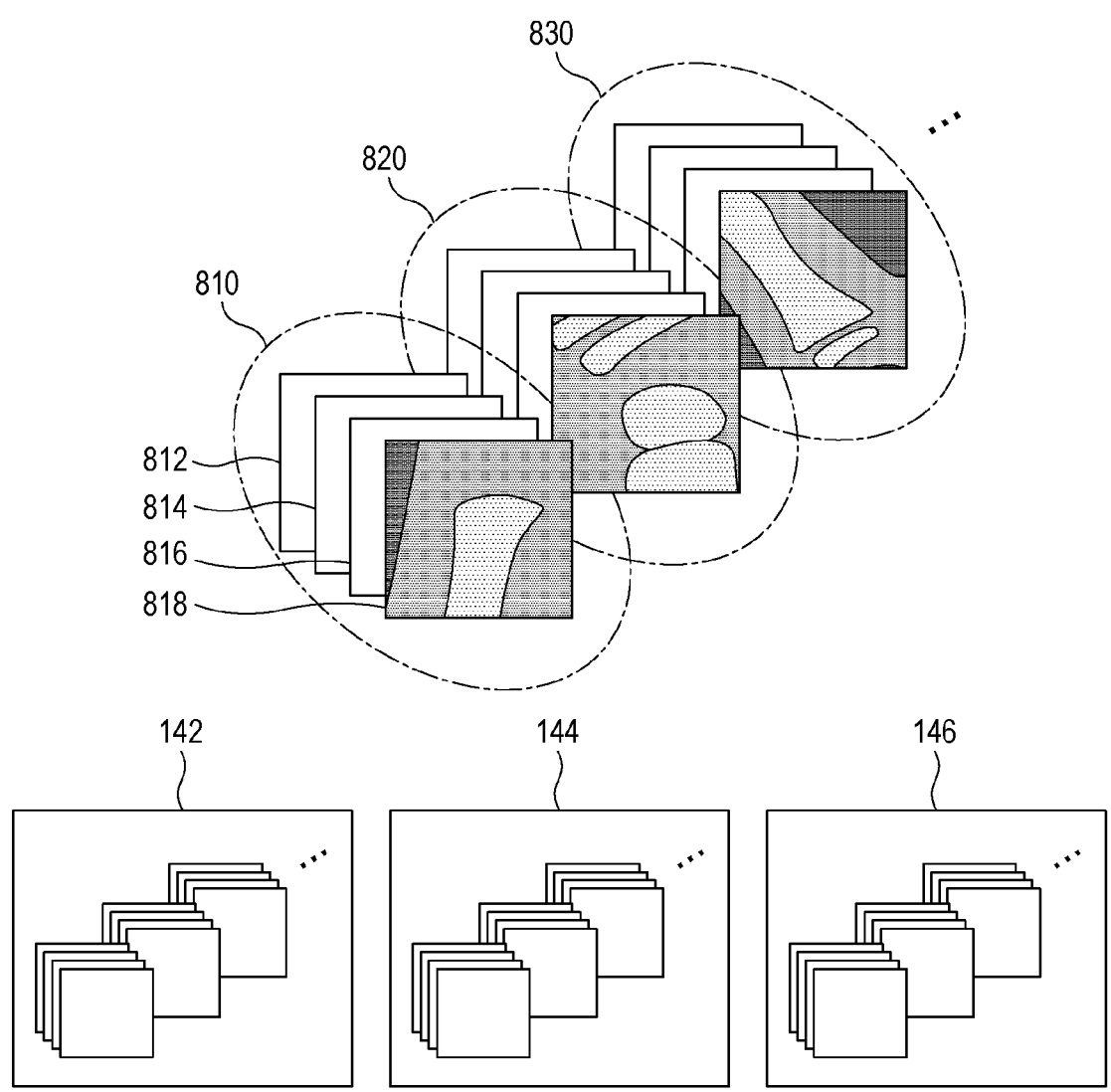
FIG. 8 illustrates a plurality of reference image sets according to an embodiment of the present disclosure.

FIG. 8 illustrates a plurality of reference image sets according to an embodiment of the present disclosure. The memory 220 may store a plurality of reference image sets. As described above, each of the reference image sets may be a set of reference images classified according to a specific race and/or a gender. One reference image set may include reference images for a plurality of body parts and a plurality of bone ages in the corresponding race and/or gender.

One reference image set may include reference images for each of a plurality of body parts. For example, one reference image set may include reference images 810 for a first body part, reference images 820 for a second body part, and reference images 830 for a third body part. The illustrated reference images are exemplary, and the first, second and third body parts are not limited to the body parts indicated by the illustrated reference images.

Further, in one reference image set, the reference images 810 for one body part (e.g., a first body part) may include reference images 812, 814, 816, 818 and the like for bone ages of the corresponding body part. For example, one reference image set may include a reference image 812 corresponding to a bone age of 5 years old of the first body part, a reference image 814 corresponding to a bone age of 6 years old of the first body part, a reference image 816 corresponding to a bone age of 7 years old of the first body part, a reference image 818 corresponding to a bone age of 8 years old of the first body part, and the like.

The memory 220 may include a plurality of such reference image sets 142, 144 and 146. As in the reference image set described above, each of the reference image sets may include reference images for each body part and for each bone age of each body part. Each of the reference image sets may include reference images representing bone shapes of a human body for one race and/or one gender. For example, one reference image set 142 may be a set of reference images for each body part and for each bone age of each body part of a black female. In addition, other reference image sets 144 and 146 may be a set of reference images for each body part and for each bone age of each body part of a Germanic male and a Han Chinese female, respectively.

In one embodiment, the input device 230 may receive race information and/or gender information for a human body as an inspection target from a user. The processor 210 may determine one reference image set from among the plurality of reference image sets stored in the memory 220 based on the race information and/or gender information received from the user. The determined reference image set is a reference image set including reference images according to the received race information and/or gender information, and may include, for example, reference images to be compared with the first segmented image.

Figure 9:
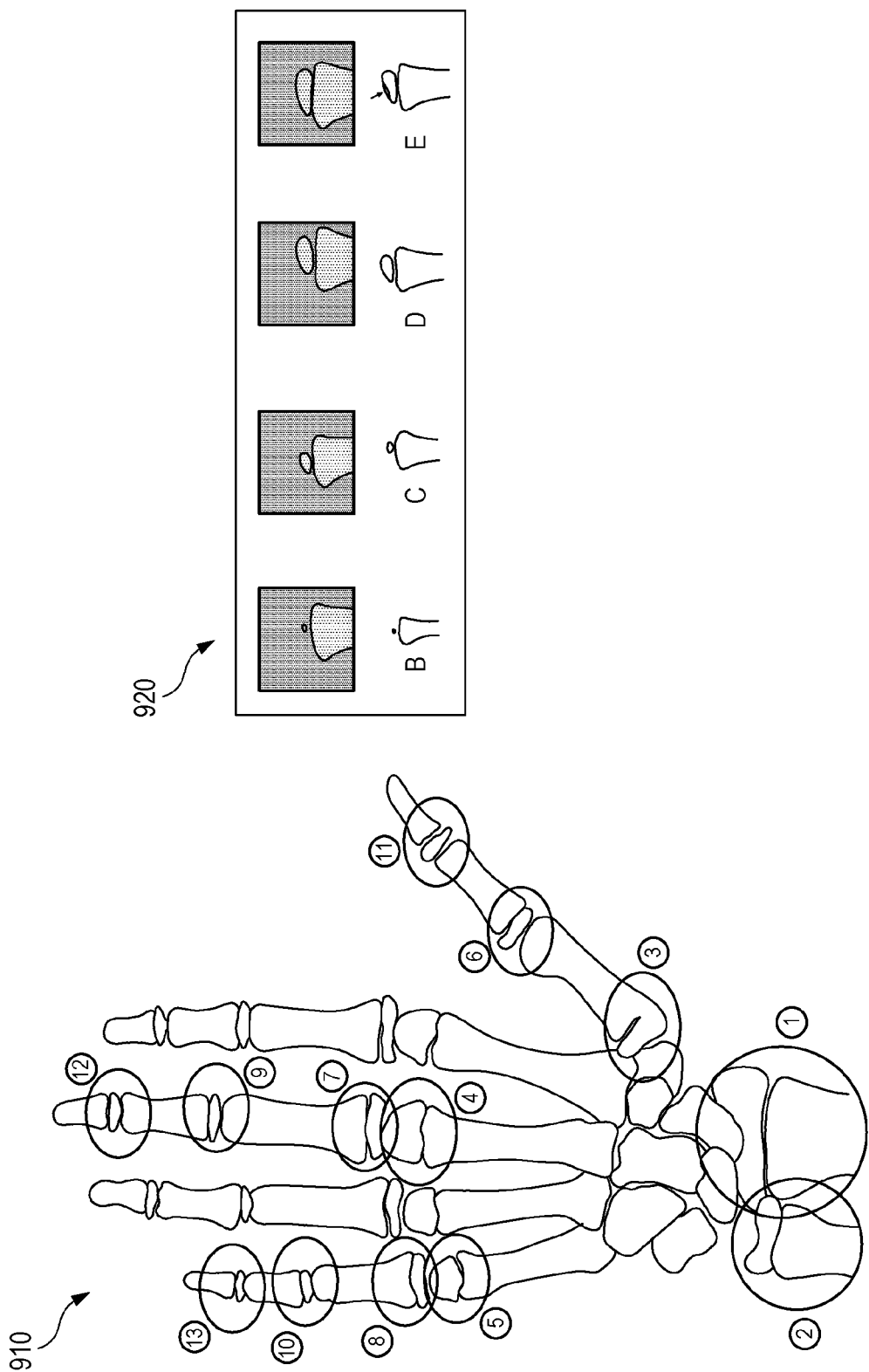
FIG. 9 illustrates reference images for a plurality of body parts and bone age grades for each body part, according to an embodiment of the present disclosure.

FIG. 9 illustrates reference images for a plurality of body parts and bone age grades for each body part, according to an embodiment of the present disclosure. As described above, the human body (e.g., the hand) may include major body parts that can affect the bone age assessment for the human body (910). The illustrated human body 910 may have 13 main body parts that are to be subjected to image comparison for determining a bone age. The selection and the number of body parts to be subjected to image comparison may be changed in some embodiments, and are not limited to the illustrated embodiment.

As described above, one reference image set may include reference images for bone ages of a plurality of body parts. For example, one reference image set may include reference images for bone ages of body part ① in the human body (920). According to the bone growth process of the corresponding body part, the reference images 920 may represent the shapes of the corresponding body part for individual grades (e.g., B to E). If a matching partial region is found by comparing the reference image having the C grade and the input image (or the segmented image), it can be determined that the corresponding partial region represents body part ① and has a bone age corresponding to the C grade.

FIG. 10 illustrates a bone age assessment method that may be performed by the electronic apparatus 200 according to an embodiment of the present disclosure. Although the respective steps of the method or algorithm according to the present disclosure have been described in a sequential order in the illustrated flowchart, the respective steps may be performed in an order that can be arbitrarily combined by the present disclosure, in addition to being performed sequentially. The description in accordance with this flowchart does not exclude making changes or modifications to the method or algorithm, and does not imply that any step is necessary or desirable. In one embodiment, at least some of the steps may be performed in parallel, repetitively or heuristically. In one embodiment, at least some of the steps may be omitted, or other steps may be added.

The electronic apparatus 200 according to the present disclosure may perform a bone age assessment method according to various embodiments of the present disclosure. The bone age assessment method according to an embodiment of the present disclosure may include dividing an input image into a plurality of segmented images (S1010), determining a first segmented image from the segmented images (S1020), processing each pixel of the first segmented image based on a reference value (S1030), selecting a first reference image for a first body part of a human body from a reference image set (S1040), determining whether or not a partial region matching the first reference image exists in the first segmented image based on calculation results for each pixel of the first segmented image and each pixel of the first reference image (S1050), determining a bone age grade of the first body part upon determining that the partial region exists (S1060), and/or determining a bone age of the human body based on the bone age grade (S1070).

In S1010, the processor 210 of the electronic apparatus 200 may divide the input image for the human body into the plurality of segmented images. In S1020, the processor 210 may determine, from the segmented images, a first segmented image having a highest priority for the first body part among a plurality of body parts. In S1030, the processor 210 may process each of the first pixels of the first segmented image based on the reference value determined from all the pixels of the input image. In S1040, the processor 210 may select the first reference image for the first body part from the reference image set including a plurality of reference images for each of the plurality of body parts. In S1050, the processor 210 may calculate each of the first pixels of the first segmented image processed by the reference value and each of the second pixels of the first reference image corresponding to the first pixels. Based on the calculation result for each of the pixels, the processor 210 may determine whether or not a partial region matching the first reference image exists in the first segmented image processed by the reference value. In S1060, upon determining that the partial region exists, the processor 210 may determine a bone age grade of the first body part represented by the partial region based on the first reference image. In S1070, the processor 210 may determine the bone age of the human body based on the determined bone age grade.

In one embodiment, processing each of the first pixels of the first segmented image (S1030) may include processing each of the first pixels of the first segmented image by setting the pixel value of each of the first pixels of the first segmented image, which is smaller than the reference value, to 0 and setting the pixel value of each of the first pixels of the first segmented image, which is equal to or larger than the reference value, to a difference value between the pixel value and the reference value. In one embodiment, the reference value may be an average value of all of the pixels of the input image.

In one embodiment, determining whether or not a partial region matching the first reference image exists (S1050) may include multiplying, by the processor 210, a pixel value of each pixel of the partial region of the first segmented image processed by the reference value and a pixel value of each pixel of the first reference image that corresponds to the each pixel of the partial region, determining a matching score by summing the multiplied pixel values for the partial region, and/or determining that the partial region matches the first reference image upon determining that the matching score is equal to or larger than a preset value.

In one embodiment, the bone age assessment method may further include determining, by the processor 210, a bone age grade of a second body part using a second segmented image having a highest priority for a second body part among the plurality of body parts and a second reference image for the second body part in the reference image set, and/or determining a bone age of the human body based on the bone age grade of the first body part and the bone age grade of the second body part.

In one embodiment, the bone age assessment method may further include determining, by the processor 210, whether or not a partial region exists using a third segmented image having a priority next to the first segmented image for the first body part and the first reference image, upon determining that the partial region does not exist.

In one embodiment, the bone age assessment method may further include adjusting, by the processor 210, the reference value upon determining that a partial region does not exist, processing each of the first pixels of the first segmented image based on the adjusted reference value, and/or determining whether or not a partial region exists using the first segmented image processed by the adjusted reference value and the first reference image.

In one embodiment, the bone age assessment method may further include determining, by the processor 210, a reference image set to be compared with the first segmented image from among the plurality of reference image sets based on race information and/or gender information inputted from a user. In one embodiment, the bone age assessment method may further include receiving, by the input device 230, race information and/or gender information for the human body as a bone age assessment target from a user. In one embodiment, the memory 220 may store a plurality of reference image sets according to races and/or genders.

Various embodiments of the present disclosure may be implemented as software recorded on a machine-readable recording medium. The software may be software for implementing the various embodiments of the present disclosure described above. The software may be inferred from various embodiments of the present disclosure by programmers in the art to which the present disclosure belongs. For example, the software may be instructions (e.g., code or code segments) or programs that can be read by a device. The device is a device capable of operating according to instructions called from a recording medium, and may be, for example, a computer. In one embodiment, the device may be the electronic apparatus 200 according to embodiments of the present disclosure. In an embodiment, the processor of the device may execute the called instructions so that components of the device can perform a function corresponding to the instructions. In one embodiment, the processor may be the processor 210 according to the embodiments of the present disclosure. The recording medium may refer to any type of device-readable recording medium in which data is stored. The recording medium may include, for example, a ROM, a RAM, a CD-ROM, a magnetic tape, a floppy disk, an optical data storage device, and the like. In one embodiment, the recording medium may be the memory 220. In one embodiment, the recording medium may be implemented in a distributed form in computer systems connected by a network. The software may be distributed, stored and executed in a computer system or the like. The recording medium may be a non-transitory recording medium. The non-transitory recording medium refers to a tangible medium irrespective of whether data is stored semi-permanently or temporarily, and does not include a signal propagating in a transitory manner.

Although the technical content of the present disclosure has been described by the examples described in some embodiments and illustrated in the accompanying drawings, it should be noted that various substitutions, modifications, and changes can be made without departing from the scope of the present disclosure which can be understood by those having ordinary skill in the art to which the present disclosure pertains. In addition, it should be noted that such substitutions, modifications and changes are intended to fall within the scope of the appended claims.

What is claimed is:

1. An electronic apparatus, comprising:
    a memory configured to store a reference image set including a plurality of reference images for a plurality of body parts; and
    a processor communicatively connected to the memory, and configured to:
    equally divide an input image capturing a human body into a preset number of segmented images;
    determine a first segmented image having a highest priority for a first body part of the plurality of body parts from the preset number of segmented images;
    determine an average value of all of pixels of the input image as a reference value;
    compare each of pixel values of first pixels of the first segmented image with the reference value;
    process the first segmented image by resetting each of the pixel values of the first pixels of the first segmented image, which is smaller than the reference value, to 0 and resetting each of the pixel values of the first pixels of the first segmented image, which is equal to or larger than the reference value, to a difference value between each of the pixel values and the reference value;
    select a first reference image for the first body part from the reference image set;
    determine whether or not a partial region matching the first reference image exists in the first segmented image processed by the reference value, based on calculation results for the first pixels of the first segmented image processed by the reference value and second pixels of the first reference image corresponding to the first pixels;
    upon determining that the partial region exists, determine a bone age grade of the first body part based on the first reference image; and
    determine a bone age of the human body based on the bone age grade.

2. The electronic apparatus of claim 1, wherein the processor is further configured to:
    multiply a pixel value of each pixel of the partial region and a pixel value of each pixel of the first reference image that corresponds to the each pixel of the partial region;
    determine a matching score by summing the multiplied pixel values for the partial region; and
    upon determining that the matching score is equal to or larger than a preset value, determine that the partial region matches the first reference image.

3. The electronic apparatus of claim 1, wherein the processor is further configured to:

determine a bone age grade of a second body part using a second segmented image having a highest priority for the second body part among the body parts and a second reference image for the second body part in the reference image set; and determine the bone age of the human body based on the bone age grade of the first body part and the bone age grade of the second body part.

4. The electronic apparatus of claim 1, wherein the processor is further configured to:

upon determining that the partial region does not exist, determine whether or not the partial region exists using a third segmented image having a priority next to the first segmented image for the first body part and the first reference image.

5. The electronic apparatus of claim 1, wherein the processor is further configured to:

upon determining that the partial region does not exist, adjust the reference value;

process each of the first pixels of the first segmented image based on the adjusted reference value; and determine whether or not the partial region exists using the first segmented image processed by the adjusted reference value and the first reference image.

6. The electronic apparatus of claim 1, wherein the memory is further configured to store a plurality of reference image sets according to races and genders, and wherein the processor is further configured to:

determine the reference image set to be compared with the first segmented image from among the plurality of reference image sets, based on race information and gender information inputted from a user.

7. The electronic apparatus of claim 1, wherein the processor is further configured to:

determine the bone age grade of the first body part according to a TW3 (Tanner-Whitehouse 3rd edition) method.

8. A method, comprising:

equally dividing an input image capturing a human body into a preset number of segmented images;

determining a first segmented image having a highest priority for a first body part of a plurality of body parts from the preset number of segmented images;

determining an average value of all of pixels of the input image as a reference value;

comparing each of pixel values of first pixels of the first segmented image with the reference value;

processing the first segmented image by resetting each of the pixel values of the first pixels of the first segmented image, which is smaller than the reference value, to 0 and resetting each of the pixel values of the first pixels of the first segmented image, which is equal to or larger than the reference value, to a difference value between each of the pixel values and the reference value;

selecting a first reference image for the first body part from a reference image set including a plurality of reference images for each of the body parts;

determining whether or not a partial region matching the first reference image exists in the first segmented image processed by the reference value, based on calculation results for the first pixels of the first segmented image processed by the reference value and second pixels of the first reference image corresponding to the first pixels;

upon determining that the partial region exists, determining a bone age grade of the first body part based on the first reference image; and determining a bone age of the human body based on the bone age grade.

9. The method of claim 8, wherein determining whether or not the partial region matching the first reference image exists includes:

multiplying a pixel value of each pixel of the partial region and a pixel value of each pixel of the first reference image that corresponds to the each pixel of the partial region;

determining a matching score by summing the multiplied pixel values for the partial region; and upon determining that the matching score is equal to or larger than a preset value, determining that the partial region matches the first reference image.

10. A non-transitory computer-readable recording medium that stores a program to be executed on a computer, wherein the program includes executable instructions for, when executed by a processor, causing the processor to perform:

equally dividing an input image capturing a human body into a preset number of segmented images;

determining a first segmented image having a highest priority for a first body part of a plurality of body parts from the preset number of segmented images;

determining an average value of all of pixels of the input image as a reference value;

comparing each of pixel values of first pixels of the first segmented image with the reference value;

processing the first segmented image by resetting each of the pixel values of the first pixels of the first segmented image, which is smaller than the reference value, to 0 and resetting each of the pixel values of the first pixels of the first segmented image, which is equal to or larger than the reference value, to a difference value between each of the pixel values and the reference value;

selecting a first reference image for the first body part from a reference image set including a plurality of reference images for each of the body parts;

determining whether or not a partial region matching the first reference image exists in the first segmented image processed by the reference value, based on calculation results for the first pixels of the first segmented image processed by the reference value and second pixels of the first reference image corresponding to the first pixels;

upon determining that the partial region exists, determining a bone age grade of the first body part based on the first reference image; and determining a bone age of the human body based on the bone age grade.

11. The recording medium of claim 10, wherein determining whether or not the partial region matching the first reference image exists includes:

multiplying a pixel value of each pixel of the partial region and a pixel value of each pixel of the first reference image that corresponds to the each pixel of the partial region;

determining a matching score by summing the multiplied pixel values for the partial region; and upon determining that the matching score is equal to or larger than a preset value, determining that the partial region matches the first reference image.

12. The recording medium of claim 10, wherein the program includes executable instructions for, when executed by the processor, causing the processor to further perform:

upon determining that the partial region does not exist, determining whether or not the partial region exists using a third segmented image having a priority next to the first segmented image for the first body part and the first reference image.

13. The recording medium of claim 10, wherein the program includes executable instructions for, when executed by the processor, causing the processor to further perform:
   upon determining that the partial region does not exist, adjusting the reference value;
   processing each of the first pixels of the first segmented image based on the adjusted reference value; and
   determining whether or not the partial region exists using the first segmented image processed by the adjusted reference value and the first reference image.

* * * * *